May 5, 1964 D. L. ARMSTRONG Plant Pat. 2,399
PEACH TREE
Filed April 30, 1963
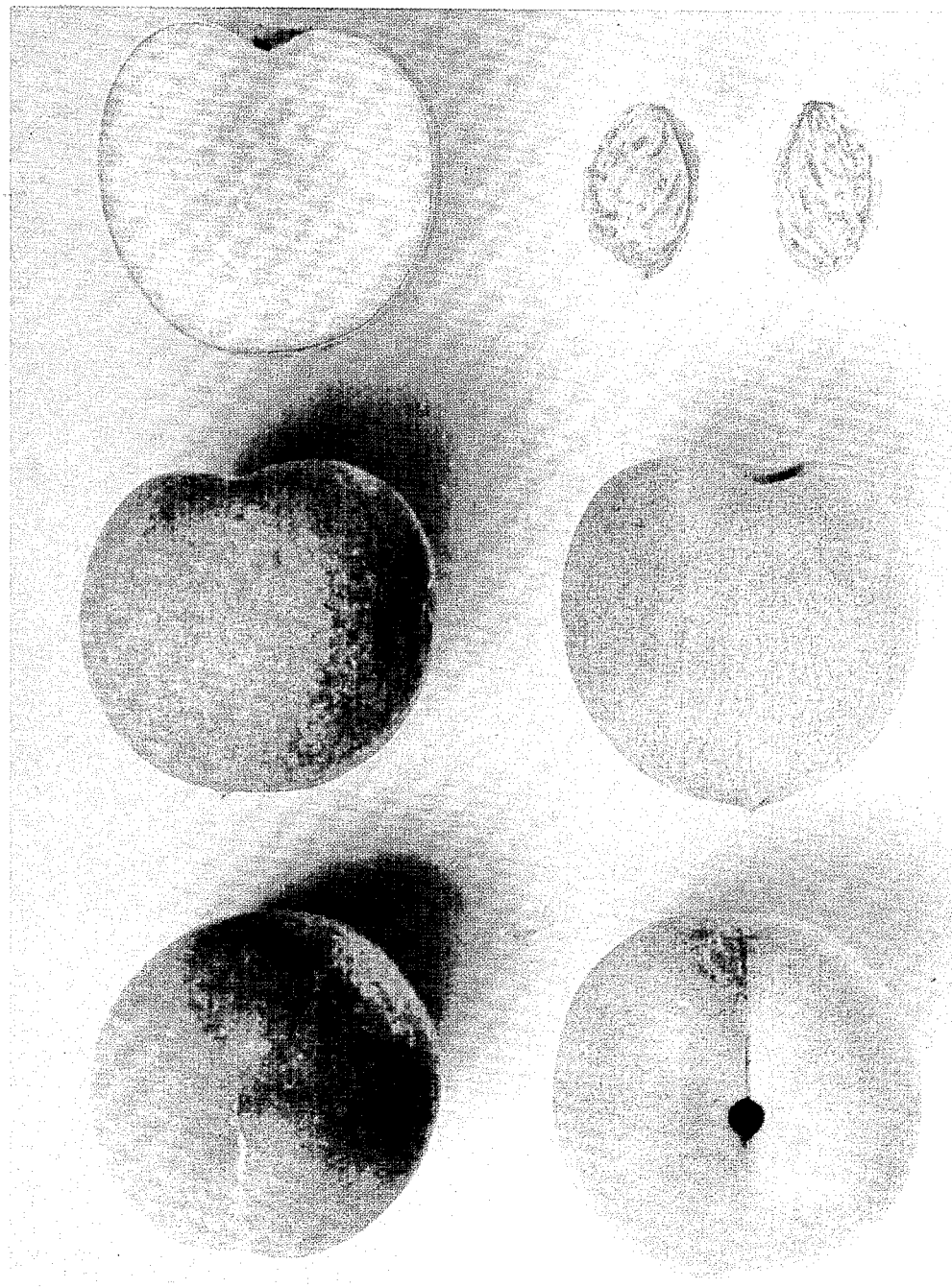
Inventor.
D. L. Armstrong
By: Robb & Robb
Attorneys.

United States Patent Office

Plant Pat. 2,399
Patented May 5, 1964

2,399
PEACH TREE

David L. Armstrong, Ontario, Calif., assignor to Armstrong Nurseries, Inc., Ontario, Calif., a corporation of California Filed Apr. 30, 1963, Ser. No. 277,054
1 Claim. (Cl. Plt.—43)

The present invention relates to a new and distinct variety of peach tree of the yellow-fleshed, freestone, fruit-bearing type, which was originated by me by crossing two unnamed and unpatented peach varieties derived from a cross of the variety "Flamingo" (Plant Patent No. 661) × "Springtime" (Plant Patent No. 1,268).

The primary objective of this breeding was to produce an improved variety of peach tree characterized by bearing yellow-fleshed fruit which has a very early ripening habit. This objective was fully achieved along with other improvements, as evidenced by the following unique combination of characteristics which distinguish the new variety from its parents, as well as from all other varieties of which I am aware:

(1) A vigorous habit of growth, with a chilling requirement about equal to that of the variety "June Gold" (Plant Patent No. 1,884);

(2) A habit of bearing large fruit crops;

(3) A very early fruit-ripening habit, ranging from a few days earlier to a week later than the variety "Springtime," as observed at Wasco, California, over a period of years, said fruit being well colored by the time it is hard-ripe, with the skin being attractively mottled and blushed with red over a yellow base color and showing little or no greenish tinge;

(4) A very attractive, uniform, symmetrical, nearly round fruit shape, with little or no beak and a relatively insignificant and smooth suture line;

(5) An attractive yellow flash color of the fruit, with no trace of red at the stone, and with the medium stone adhering rather tightly to the flesh, but becoming free when the fruit is fully ripe; and (6) A particularly good fruit quality and flavor approaching that of mid-season type peaches.

The unnamed parent varieties were sister seedlings, with the seed parent being a yellow-fleshed, freestone peach variety which was very productive and had a moderately low chilling requirement, with the fruit ripening a few days after the variety "July Elberta" (Plant Patent No. 15), and the fruit being large, well-shaped and having a moderate red blush, while being of very good quality and flavor. As distinguished from this parent, the new variety ripens earlier, from 6 to 7 weeks ahead, with the fruit being somewhat smaller and having more red coloring.

The pollen parent was a very productive yellow-fleshed, freestone peach variety, with a chilling requirement slightly higher than the variety "June Gold," the fruit of which was of medium size, symmetrical and nearly round, with a very attractive red blush or mottle, and ripening a few days after the variety "June Gold." As compared with this parent, the fruit of the new variety ripens from two and a half (2½) to three (3) weeks earlier, and the fruit is of slightly smaller size.

In comparison with its ancestor "Springtime," the principal distinction resides in the fact that the fruit of the new variety is yellow-fleshed, while that of "Springtime" is white-fleshed.

The new variety is also distinguished from its ancestor "Flamingo" by the smaller size of its fruit and its much earlier ripening period, contrary to the mid-season ripening period of "Flamingo."

As compared with other varieties having a similar ripening period, such as the variety "Mayflower" (unpatented), the fruit of the new variety is yellow-fleshed, while the other varieties are white-fleshed.

Asexual reproduction of my new variety by budding, as performed by me at Wasco, California, shows that the foregoing characteristics and distinctions come true to form and are established and transmitted through succeeding propagations.

The accompanying drawings show typical specimens of the fruit and stones of my new variety, with both exterior and sectional views of the fruit being shown, and all of said views being depicted in color as nearly true as is reasonably possible to make the same in a color illustration of this character.

The following is a detailed description of my new variety, as based upon observations of specimens grown at Wasco, California, with color terminology in accordance with Robert F. Wilson's Horticultural Color Chart (hereinafter abbreviated as "Wilson") and Ridgway's Color Standards and Nomenclature (hereinafter abbreviated as "Ridgway"), except where general color terms of ordinary dictionary significance are obvious:

*Tree*

Habit: Vigorous; upright-spreading.

Chilling requirement: Moderately low; about equal to that of "June Gold."

Fruit production: Bears very heavy crops at Wasco, California; considerable thinning is necessary.

Current growth:

*Surface texture.*—Smooth at first, with lenticels small and minute; some larger, cracked and slightly raised lenticels appear with age toward the base of the more vigorous shoots.

*Color.*—Green at first, but reddish on exposed surfaces, with lenticels appearing as small, nearly white dots; all becoming more brown with age.

Two-year wood:

*Surface texture.*—Generally smooth, with slight, raised, irregular, longitudinal striations and numerous lenticels.

*Color.*—Brown.

Old wood:

*Surface texture.*—Generally smooth, with moderate number of large, raised lenticels, and some small longitudinal fissures.

*Color.*—From grey to greyish-brown or reddish-brown on more exposed surfacse.

Leaves:

*Size.*—Length—from 6 inches to 7½ inches. Width—from 1¼ inches to 1½ inches.

*Shape.*—Lanceolate, with apex acuminate.

*Color (mature).*—Upper surface—near Forest Green, Plate XVII (Ridgway). Under surface—near Chromium Green, Plate XXXII (Ridgway).

*Petiole.*—Medium length; from thick to medium thickness.

*Margin.*—Finely serrate; glandular.

*Glands.*—Reniform; large size; at least 3, but often from 4 to 6 in number; borne both on the petiole and on the base of the blade.

Vegetative buds:

*Size.*—Small.

*Shape.*—Ovoid, unless compressed between flower buds.

*Scales.*—Thick pubescence; moderate length.

*Color.*—Dark brown.

*Flowers*

Dates of first and full bloom: Over prolonged period of observations, first bloom varied from February 22 to March 7, and full bloom varied from March 5 to March 17, due to weather variations from year to year.

Dormant flower buds:

*Shape.*—Ovoid.

*Scales.*—Pubescent.

*Color.*—Dark brown, with pubescence giving a whitish effect.

Size (when fully open): Non-showy; large; about 1 inch in diameter.

Petatlage: Single; usually 5 petals.

Form: Cupped.

Color (open flower): Near China Rose, Plate 024/3, page 111 (Wilson).

*Fruit*

Ripening dates: Generally ripens from about mid-May until about late May at Wasco, California; over prolonged period of observations, the dates of first ripening ranged from May 10 to May 26; usually ripens in the general period of the peach variety "Springtime," ranging from a few days earlier to as much as 5 days to a week later than the ripening of that variety.

Maturity when described: Eating ripe.

Size: Generally from small to medium size.

*Axial diameter.*—From 2 inches to 2¼ inches.

*Transverse diameter in suture plane.*—From 2 inches to 2⅜ inches.

*Transverse diameter at right angles to suture plane.*—From 2 to 2⅜ inches.

Form: Relatively uniform; nearly symmetrical; globose.

Suture: Generally shallow and insignificant, extending from base to apex; slight depression beyond pistil point.

Ventral surface: Rounded, but sometimes slightly lipped toward base and apex, and often not lipped at all.

Stem cavity: Somewhat rounded; elongated in suture plane; with suture showing on one side.

*Depth.*—About ¼ inch to ⅜ inch.

*Width.*—About ½ inch to ¾ inch.

Base: From rounded to truncate.

Apex: Short; insignificant; apical pistil point.

Stem: Medium caliper; glabrous; from medium to weak adherence to stone. Length—about ½ inch.

Skin:

*Thickness.*—From medium to thin.

*Texture.*—Medium.

*Tenacity to flesh.*—Free.

*Pubescence.*—From moderate to scant; short.

*Color.*—Ground color varies from near Lemon Yellow, Plate 4/2, page 4 (Wilson) to near Indian Yellow, Plate 6/2, page 6 (Wilson), all blushed or mottled with from near Delft Rose, Plate 020/1, page 108 (Wilson) to near Claret Rose, Plate 021, page 109 (Wilson).

Flesh:

*Quality.*—Medium firmness; melting; few tender fibres.

*Aroma.*—Pronounced.

*Flavor.*—Good balance between sugar and acid, with distinctive peach flavor more characteristic of mid-season types.

*Color.*—Between Buttercup Yellow, Plate 5/2, page 5 (Wilson) and Buttercup Yellow, Plate 5/3, page 5 (Wilson), blending with near Lemon Yellow, Plate 4/1, page 4 (Wilson) toward pit: occasionally, though not usually, some small specks of near Geranium Lake, Plate 20, page 20 (Wilson) are present; surface of pit cavity is between Lemon Yellow, Plate 4, page 4 (Wilson) and Lemon Yellow, Plate 4/2, page 4 (Wilson).

Stone:

*Tenacity of flesh.*—Basically free, but because of early ripening, stone adheres to flesh quite strongly until the fruit is fully ripe when it becomes quite free.

*Size.*—Medium. Length — about 1¼ inches. Width—from about ¾ inch to about ⅞ inch. Thickness—from about ⅝ inch to about ¾ inch.

*Form.*—Ovoid; cuneate toward apex.

*Base.*—Somewhat oblique.

*Hilum.*—Oblong.

*Apex.*—From rounded to acuminate.

*Sides.*—Slightly unequal; irregularly furrowed toward apex and sometimes near base; pitted from base to past center.

*Ventral edge.*—Medium thickness; generally without wing.

*Dorsal edge.*—Medium; shallow groove toward base; ridges on either side interrupted.

*Color.*—Between Light Pinkish Cinnamon, Plate XXIX (Ridgway) and Cinnamon, Plate XXIX (Ridgway).

I claim:

A new and distinct variety of peach tree of the yellow-fleshed, freestone, fruit-bearing type, substantially as herein shown and described, characterized particularly as to novelty by the unique combination of a vigorous habit of growth, a chilling requirement about equal to that of the peach variety "June Gold" (Plant Patent No. 1,884), a habit of bearing large fruit crops, a very early fruit-ripening habit ranging from a few days earlier to a week later than the peach variety "Sprnigtime" (Plant Patent No. 1,268), said fruit being well colored by the time it is hard-ripe, with the fruit skin being attractively mottled and blushed with red over a yellow base color and showing little or no greenish tinge, a very attractive, uniform, symmetrical, nearly round fruit shape, with little or no beak and relatively insignificant and smooth suture line, an attractive yellow flesh color of the fruit, with no trace of red at the stone and with the medium stone adhering rather tightly to the flesh until the fruit is fully ripe when the stone becomes free, and a particularly good fruit quality and flavor approaching that of mid-season type peaches.

No references cited.